(12) United States Patent
Fischer

(10) Patent No.: US 8,313,493 B2
(45) Date of Patent: Nov. 20, 2012

(54) HYDRAULIC GUIDEWIRE ADVANCEMENT SYSTEM

(75) Inventor: Frank J. Fischer, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1106 days.

(21) Appl. No.: 12/170,923

(22) Filed: Jul. 10, 2008

(65) Prior Publication Data

US 2010/0010499 A1    Jan. 14, 2010

(51) Int. Cl.
*A61F 11/00*    (2006.01)
(52) U.S. Cl. .................... 606/108; 604/164.13
(58) Field of Classification Search ............ 606/108; 604/95.01, 95.02, 95.03, 96.01, 164.01, 164.12–164.13, 604/194, 523, 528, 532
See application file for complete search history.

(56) References Cited

U.S. PATENT DOCUMENTS

| | | | |
|---|---|---|---|
| 3,952,747 A * | 4/1976 | Kimmell, Jr. ............. 606/195 |
| 4,102,410 A * | 7/1978 | Ross ........................ 173/133 |
| 4,246,902 A * | 1/1981 | Martinez ................... 604/22 |
| 4,854,325 A * | 8/1989 | Stevens .................... 600/434 |
| 4,898,575 A * | 2/1990 | Fischell et al. ............. 604/22 |
| 4,950,238 A * | 8/1990 | Sullivan ..................... 604/22 |
| 5,273,052 A * | 12/1993 | Kraus et al. .............. 600/585 |
| 5,419,774 A * | 5/1995 | Willard et al. .............. 604/22 |
| 5,458,573 A | 10/1995 | Summers |
| 5,626,603 A | 5/1997 | Venturelli et al. |
| 5,749,371 A | 5/1998 | Zadini et al. |
| 5,807,330 A * | 9/1998 | Teitelbaum .............. 604/96.01 |
| 5,817,101 A | 10/1998 | Fiedler |
| 5,853,384 A * | 12/1998 | Bair ........................... 604/22 |
| 5,971,949 A | 10/1999 | Levin et al. |
| 5,989,263 A * | 11/1999 | Shmulewitz ............. 606/108 |
| 6,004,284 A * | 12/1999 | Sussman et al. ............ 604/27 |
| 6,113,608 A | 9/2000 | Monroe et al. |
| 6,152,931 A | 11/2000 | Nadal et al. |
| 6,162,195 A | 12/2000 | Igo et al. |
| 6,183,420 B1 * | 2/2001 | Douk et al. .............. 600/462 |
| 6,264,661 B1 * | 7/2001 | Jerger et al. ............. 606/100 |
| 6,273,861 B1 * | 8/2001 | Bates et al. .............. 600/567 |
| 6,325,777 B1 * | 12/2001 | Zadno-Azizi et al. ..... 604/97.01 |
| 6,348,040 B1 * | 2/2002 | Stalker et al. ............ 600/585 |
| 6,743,208 B1 * | 6/2004 | Coyle ..................... 604/164.13 |
| 7,141,041 B2 | 11/2006 | Seward |

(Continued)

OTHER PUBLICATIONS

International Search Report and Written Opinion of the International Searching Authority for International Application No. PCT/US2009/049773, dated Oct. 10, 2009, 8 pages.

*Primary Examiner* — Gary Jackson
*Assistant Examiner* — Erin Colello
(74) *Attorney, Agent, or Firm* — Brinks Hofer Gilson & Lione

(57) ABSTRACT

A hydraulic guidewire advancement system for enhancing access through lesions or occlusions in distal regions of a patient's vasculature includes a catheter comprising a sheath, a guidewire lumen, and a proximal catheter port connected to a hydraulic driver. A hydraulic guidewire is coaxially disposed through the guidewire lumen, the hydraulic guidewire comprising a piston movably disposed in the guidewire lumen, the piston forming a seal with an interior surface of the sheath. The hydraulic driver is configured to generate hydraulic pressure against the piston sufficient to advance or retract the hydraulic guidewire relative to the catheter. The hydraulic driver can apply positive or negative pressure to the piston, so as to repeatedly contact and break through the lesion with the distal end of the hydraulic guidewire.

24 Claims, 4 Drawing Sheets

U.S. PATENT DOCUMENTS

| | | |
|---|---|---|
| 7,163,552 B2 | 1/2007 | Diaz |
| 7,220,269 B1 | 5/2007 | Ansel et al. |
| 7,527,636 B2 * | 5/2009 | Dunfee et al. ............... 606/200 |
| 8,043,352 B2 * | 10/2011 | Agnew ......................... 623/1.11 |
| 2003/0100911 A1 * | 5/2003 | Nash et al. ................... 606/159 |
| 2003/0125764 A1 | 7/2003 | Brady et al. |
| 2004/0064067 A1 * | 4/2004 | Ward ............................ 600/562 |
| 2004/0082879 A1 * | 4/2004 | Klint ............................ 600/585 |
| 2004/0115164 A1 * | 6/2004 | Pierce et al. ............... 424/78.35 |
| 2004/0153094 A1 * | 8/2004 | Dunfee et al. ................ 606/108 |
| 2004/0210194 A1 * | 10/2004 | Bonnette et al. ......... 604/167.06 |
| 2004/0230219 A1 * | 11/2004 | Roucher, Jr. .................. 606/194 |
| 2005/0038335 A1 | 2/2005 | Gross et al. |
| 2005/0119679 A1 * | 6/2005 | Rabiner et al. ............... 606/159 |
| 2005/0209559 A1 * | 9/2005 | Thornton et al. ......... 604/103.04 |
| 2005/0288700 A1 | 12/2005 | Chermoni |
| 2006/0009737 A1 | 1/2006 | Whiting et al. |
| 2007/0049867 A1 * | 3/2007 | Shindelman ............. 604/103.04 |
| 2007/0088380 A1 * | 4/2007 | Hirszowicz et al. .......... 606/194 |
| 2008/0015558 A1 * | 1/2008 | Harlan ............................ 606/15 |

* cited by examiner

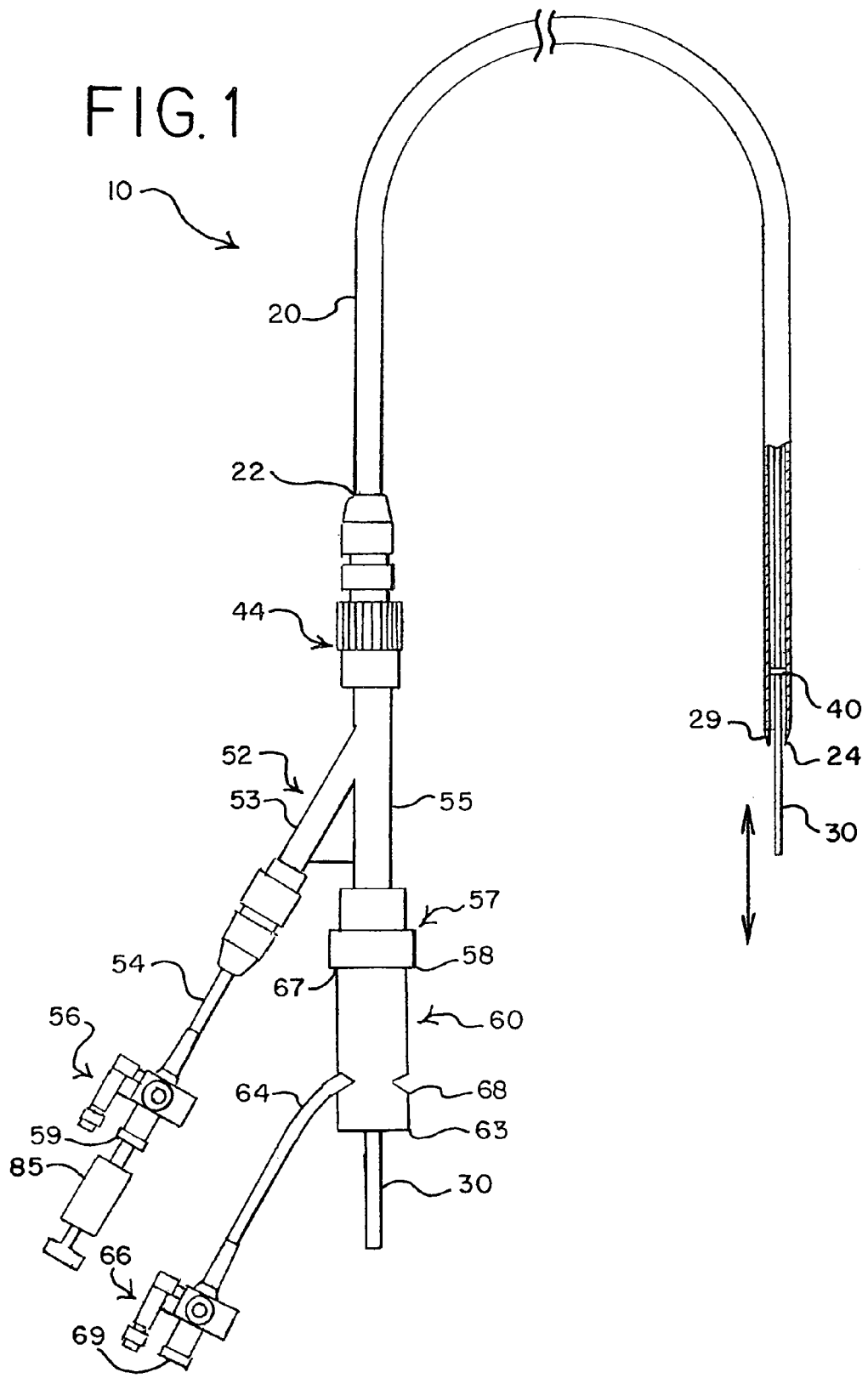

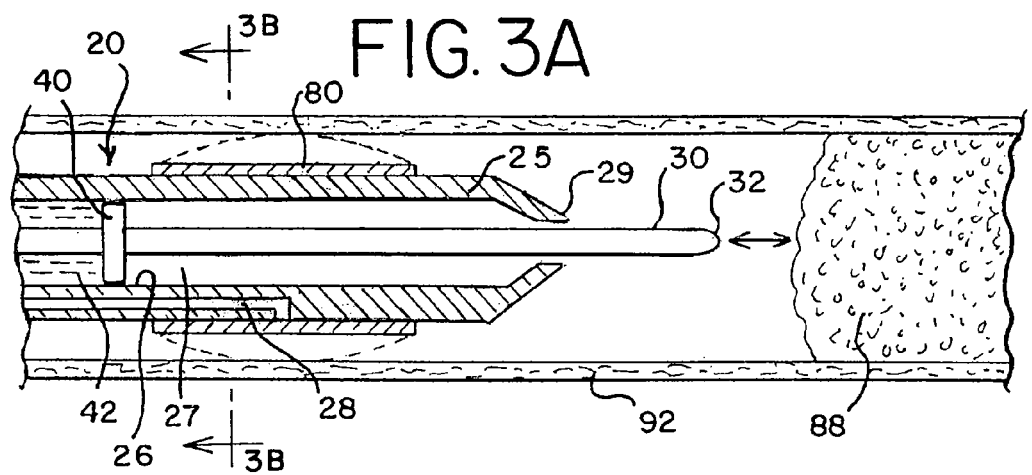
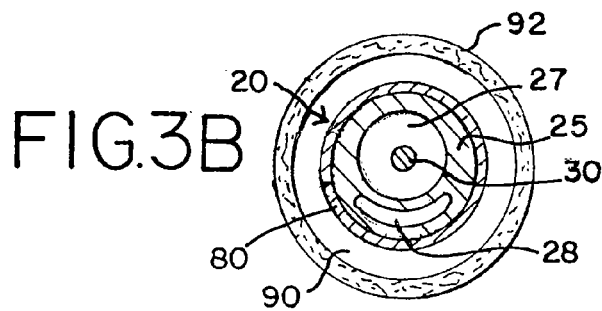

HYDRAULIC GUIDEWIRE ADVANCEMENT SYSTEM

TECHNICAL FIELD

This invention relates generally to a hydraulic guidewire advancement system for use in conjunction with angioplasty procedures, stenting procedures, and other device placement procedures and their related devices.

BACKGROUND

Guidewires are typically used to navigate the vasculature of a patient during intracorporeal procedures. Once the guidewire has been introduced, it may then be used to introduce one or more medical devices. Conventional guidewires are typically about 0.014-0.038 inches in diameter and have a lubricous coating to enhance guidewire introduction and movement. These conventional "floppy" guidewires have sufficient flexibility and torque control for navigation through tortuous vessels.

It has been estimated that a third to a half of patients presenting coronary disease from angiograms have at least one chronic total occlusion (CTO). However, conventional guidewires often lack sufficient tip stiffness or pushability to traverse the tough fibrous proximal and distal caps in a CTO, particularly when contralateral intervention procedures are employed to reach a distant CTO. In such cases, a physician may introduce a catheter through a femoral artery to access the lower leg, which necessarily increases the working length of the guidewire. Where there is a need to traverse an occlusion, such as a CTO in a peripheral or coronary artery, pushability of the device from the access site cannot provide a sufficient or predictable amount of force through the occluded region to facilitate further interventional procedures. Indeed, the major determinant of success for angioplasty of CTOs is ability to pass a guidewire across the lesion. Accordingly, there exists a need for improving the ability to maneuver a guidewire and/or catheter through lesions in distal regions of a patient's vasculature.

SUMMARY

The present invention provides a hydraulic guidewire advancement system for enhancing access through occlusions in distal regions of a patient's vasculature. In one aspect, a hydraulic guidewire advancement system includes a catheter comprising a sheath, a guidewire lumen, and a proximal catheter port connected a hydraulic driver. A hydraulic guidewire is coaxially disposed through the guidewire lumen, the hydraulic guidewire comprising a piston movably disposed in the guidewire lumen, the piston forming a seal with an interior surface of the sheath. The hydraulic driver is configured to generate hydraulic pressure against the piston sufficient to advance or retract the hydraulic guidewire relative to the catheter. The hydraulic driver can repeatedly apply positive or negative pressure to the piston, thereby advancing or retracting the hydraulic guidewire, respectively, so as to repeatedly contact (by dottering or "jackhammering") the lesion or occlusion. The catheter adds support to the protruding guidewire end and acts in conjunction with the guidewire to clear a path through the occlusion for access by other interventional devices.

Upon advancement of the distal end of the catheter through the occlusion, a hydraulic pressure release means may be employed to remove the hydraulic guidewire in exchange for a secondary guidewire (e.g., working guidewire). This may be accomplished by disengaging a seal member in a check flow adapter from the proximal end of the catheter. Upon breaking the pressure seal and exchanging the hydraulic guidewire for a secondary guidewire, additional interventional devices can be introduced over the secondary guidewire to treat the lesion or occlusion.

In another aspect, an expandable balloon is affixed to a distal portion of the catheter sheath in the above described catheter, wherein an inflation lumen extends the sheath and is in fluid communication with an interior of the balloon. The balloon can be inflated against the surrounding vessel just proximal to a lesion. This can help to center and/or stabilize the position of the catheter and hydraulic guidewire relative to the lesion.

In a further aspect, the above described catheter is coaxially disposed in a balloon catheter. The balloon catheter is defined by a lumen housing the catheter axially disposed therethrough. A balloon attached near the distal end of the balloon catheter is connected to one or more inflation lumens and is inflated against the surrounding vessel just proximal to a lesion.

In another aspect, a method for advancing a guidewire through an occlusion in a bodily lumen includes providing a hydraulic guidewire advancement system according to the present invention; connecting a hydraulic driver to a catheter port; positioning the distal catheter end in a bodily lumen proximal to the lesion; and actuating the hydraulic driver to generate a positive hydraulic pressure on the piston sufficient to advance the hydraulic guidewire distally toward the lesion. The hydraulic driver can be additionally actuated to generate a negative hydraulic pressure on the piston sufficient to retract the hydraulic guidewire away from the lesion. Through repeated advancement and retraction steps, the guidewire can be actuated to repeatedly contact the lesion. Then, by extending the distal end of the catheter sheath and the guidewire through the lesion, a path can be cleared to permit entry of additional interventional devices therethrough. A balloon may be optionally employed to aid in centering and/or stabilizing the position of the catheter and hydraulic guidewire relative to the lesion or occlusion prior to the step of contacting the lesion.

BRIEF DESCRIPTION OF THE DRAWINGS

The accompanying drawings incorporated in and forming a part of the specification illustrate several aspects of the present invention, and together with the description serve to explain the principles of the invention. In the drawings:

FIG. 1 is a side view of a hydraulic guidewire advancement system of the type described in the present invention;

FIG. 3A is a partial side sectional view of the distal end of the hydraulic guidewire advancement system according to another embodiment of the present invention;

FIG. 3B is a cross-sectional view of the hydraulic guidewire advancement system depicted in FIG. 3A and taken along line 3B-3B.

DETAILED DESCRIPTION

Figure 2A:
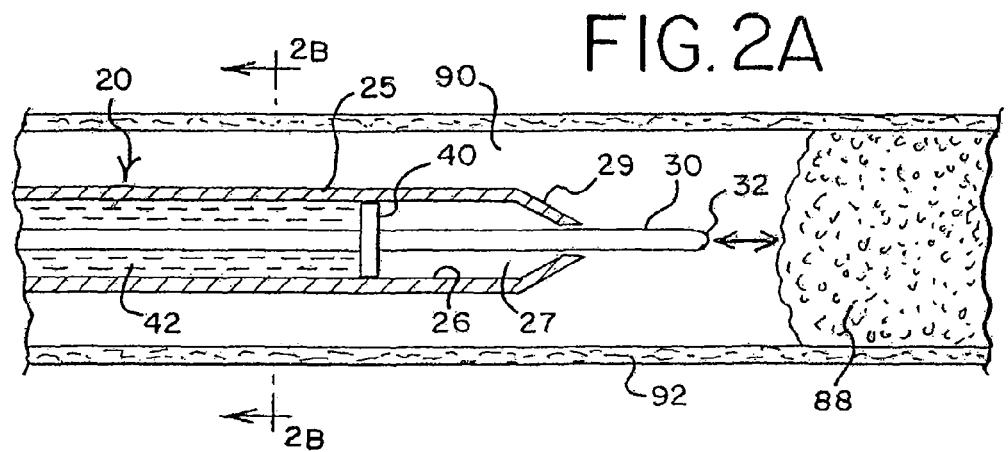
FIG. 2A is a partial side sectional view of the distal end of a hydraulic guidewire advancement system according to one embodiment of the present invention.

Turning now to the drawings, FIG. 1 depicts an exemplary hydraulic guidewire advancement system 10 in accordance with the present invention. The hydraulic guidewire advancement system 10 includes an elongated tubular member or catheter 20 and a hydraulic guidewire 30 extending longitudinally therethrough. In FIGS. 1 to 4, the catheter 20 includes a proximal end 22 and a distal end 24 and is formed as a sheath 25 having an inner surface 26 defining a guidewire lumen 27 axially disposed therethrough. Extending through the guidewire lumen 27, the hydraulic guidewire 30 is fixedly coupled to a piston 40, configured as a disk-shaped annular flange formed from a resilient material to have a diameter slightly larger than the inner diameter of the catheter 20 so as to form a movable seal through the guidewire lumen 27. In FIGS. 1 to 4, the catheter 20 is depicted as having a tapered distal end 29.

A connector 44 secures the proximal end 22 of the catheter 20. The Y-shaped adapter 52 includes a side arm 53 to which a tube 54, a three-way stopcock 56, and side port 59 are connected, and through which saline or other fluids may be passed, including hydraulic fluid for pressurizing the lumen 27 of the catheter 20. In the embodiment as illustrated, a hydraulic driver (syringe 85) is attached to side port 59. The proximal end of the primary arm 55 of the Y-shaped adapter 52 comprises a connector hub 57 threadedly connected to a check flow adapter 60, which provides a means for breaking the pressure seal within the catheter 20 and for removing the hydraulic guidewire 30.

The check flow adapter 60 includes a distal end 67 threadedly and removably connected to a connector hub 57 at the proximal end 58 of the Y-adapter 52. The proximal end 63 of the check flow adapter 60 includes a seal member 68. The seal member 68 preferably includes one or more silicone disks (not shown) for preventing the backflow of fluids therethrough. The disks typically include a slit or aperture to allow for passage of the guidewire 30 therethrough. The proximal end 63 may further include a side tube 64 to which a three-way stopcock 66 and port 69 are connected, and through which saline or other fluids may be passed. The hydraulic guidewire 30 can be extended through the proximal end 63 of the check flow adapter 60 by extending it through the seal member 68, through the Y adapter 52, through the guidewire lumen 27, and extending beyond the distal end 24 of the catheter 20. Exemplary check flow adapters that may be adapted for use in the present invention can be commercially obtained through Cook Medical, Bloomington, Ind. (for example, Check-Flo® Accessory Adapter). Although the embodiment of the catheter 20 illustrated in FIG. 1 and described above utilizes a Y-shaped adapter 52 having two separate proximal openings, it should be understood by those of skill in the art that other types of adapters could be utilized for connecting the catheter sheath 25 to the check flow adapter 60. For example, an adapter having a single proximal opening to which the check flow adaptor 60 is attached could be utilized, thereby eliminating the side arm 53 and port 59 depicted in FIG. 1.

The hydraulic guidewire advancement system 10 can be inserted in a bodily vessel 90 with an introducer needle using, for example, the well-known percutaneous vascular access technique (Seldinger). One or both of the stopcocks 56, 66 can be connected to a hydraulic driver 85, such as a syringe or other device suitable for establishing hydraulic pressure in the hydraulic guidewire advancement system 10.

Figure 2B:
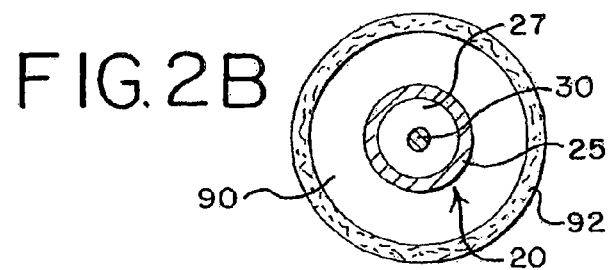
FIG. 2B is a cross-sectional view of the hydraulic guidewire advancement system depicted in FIG. 2A and taken along line 2B-2B.

FIG. 2A depicts a partial side sectional view of the distal end of the hydraulic guidewire advancement system 10 according to one embodiment of the present invention. FIG. 2B depicts a cross-sectional view of the hydraulic guidewire advancement system 10 depicted in FIG. 2A and taken along line 2B-2B. In FIG. 2A, the distal end 32 of the hydraulic guidewire 30 is shown extending through the tapered distal end 29 of the catheter 20 proximal to an occlusion 88 in a bodily vessel 90. The hydraulic guidewire 30 is coupled to a piston 40. As shown in FIG. 1, a hydraulic driver 85, such as a syringe (not shown) is connected to a port 59 in the three-way stopcock 56 of the Y-adapter 52 to supply a pressurized fluid column 42 (for example, comprised of saline) against the piston 40 to drive movement of the hydraulic guidewire 30 relative to the occlusion 88. The driver 85 can supply positive or negative pressure through the port 59 to the piston 40 so as to advance or retract the hydraulic guidewire 30, respectively. Typically, the driver 85 is actuated so that the hydraulic guidewire 30 repeatedly contacts a lesion or occlusion 88 (by dottering or "jackhammering"), for example, alternatively advancing and retracting the guidewire 30 over a distance of between about 1 mm to about 30 mm, and preferably over a distance of between about 5 mm to about 15 mm. In one exemplary method, the guidewire is advanced and retracted over a distance of about 10 mm. The distal end 29 of the catheter 20, which is maintained stationary during actuation of the hydraulic guidewire 30, adds support to the distal guidewire end 32 and acts in conjunction with the guidewire 30 to clear a path through the occlusion 88 to facilitate entry of additional interventional devices therethough.

Upon advancement of the distal end 24 of the catheter 20 through the occlusion 88, the hydraulic guidewire 30 may be removed and exchanged for a second guidewire, which may then be used to advance additional medical devices, such as balloon catheters and stent delivery systems. Alternatively, the catheter 20 and hydraulic guidewire 30 may be further advanced to another downstream occlusion 88 to repeat the above-described process for traversing the occlusion 88. In either case, after the distal end 24 of the catheter 20 has advanced distal to a desired occlusion 88, the hydraulic guidewire 30 will be typically removed and exchanged for a second guidewire (or working guidewire).

To remove the hydraulic guidewire 30, it is preferable to break the pressure seal in the hydraulic guidewire advancement system 10. This can be accomplished by rapidly disengaging the threadedly engaged check flow adapter 60 from the connector hub 57 at the proximal end 58 of the Y-adapter 52. Removal of the adapter 60 also permits the piston 40 to pass out through the proximal end of the connector 57. The pressure seal can also be broken by opening a passageway to the guidewire lumen 27 via one of the 3-way stopcocks 56, 66 depicted in FIG. 1. This can be done before or during the process of disengaging the adapter 60. In particular, negative pressure can be applied through one of the side ports 59, 69 depicted in FIG. 1 to remove the hydraulic fluid 42 prior to removing the hydraulic guidewire 30.

At any time while the hydraulic guidewire advancement system 10 is in use, negative pressure may be applied to the catheter 20 through an optional aspiration lumen (not shown) in the sheath 25 or through the guidewire lumen 27 to aid in removing debris associated with the occlusion 88. For example, aspiration may be utilized to remove a thrombus as the guidewire advancement system 10 is advanced through an occlusion 88 in the venous system. The aspiration lumen may be connected to a separate aspiration port (not shown) under vacuum pressure.

Once the seal member 68 is disengaged, the hydraulic guidewire 30 can be exchanged with a secondary guidewire (not shown) to facilitate delivery of additional interventional devices for treating the lesion or occlusion 88, including stents, atherectomy devices and the like. The secondary guidewire may be extended through the lumen 27 of the catheter 20, beyond its distal end 24. Then, while maintaining the position of the secondary guidewire in place, the catheter sheath 25 may be retracted and removed. Additional interventional devices can then be delivered along the path of the secondary guidewire by conventional over-the-wire delivery techniques to target treatment sites.

Given the variety of CTOs, which typically range between about 20 cm to about 25 cm in length in the peripheral arteries and between about 5 cm to about 8 cm in coronary arteries (with different levels of hardness and calcification), those of skill in the art will appreciate that different lesions may require different guidewire tips. Although softer tips stand a lesser chance of perforation, their tip load or stiffness may be insufficient to cross an occlusion 88. This may necessitate further recanalization attempts involving successive exchanges of the hydraulic guidewires 30 having progressively stiffer tips. Thus, guidewires exhibiting incremental increases in tip stiffness between about 3.0 to about 25.0 grams of tip load force may be employed in the hydraulic guidewires 30 of the present invention.

FIGS. 3A depicts a partial side sectional view of the distal end of the hydraulic guidewire advancement system 10 according to another embodiment of the present invention. In FIG. 3A, an expandable balloon 80 is affixed near the distal end 24 of the catheter sheath 25. In addition, an inflation lumen 28 extends through the sheath 25 (FIG. 3B), which is in fluid communication with an interior of the balloon 80. The boundaries of the balloon 80 are defined by proximal 81 and distal 82 balloon attachment sites.

In this embodiment, an additional side port (not shown) is incorporated distal to the Y adapter 52 depicted in FIG. 1. This additional side port is configured to receive pressurized fluid for inflating the balloon 80. This additional side port is in fluid communication with the inflation lumen 28 extending through the wall of the catheter sheath 25 (FIGS. 3A and 3B). The inflation lumen 28 is open to the interior of the balloon 80 to complete the fluid communication of the balloon 80 with the fluid supply. Conventional fluids, such as saline, may be supplied by a suitable driver under an inflation pressure sufficient for inflating the balloon 80 and centering the catheter 20. Radiographic contrast fluids may be included for visualization purposes. The balloon 80 can be selected to have an average burst pressure between about 2 to about 20 atmospheres, preferably between about 5 to about 10 atmospheres. Those skilled in the art may readily optimize the burst pressure to a desired level.

Figure 4A:
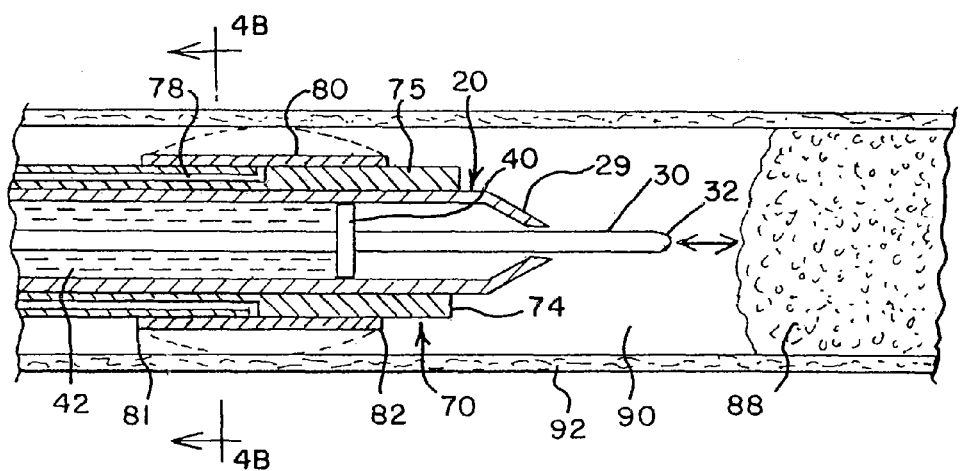
FIG. 4A is a partial side sectional view of the distal end of the hydraulic guidewire advancement system according to another embodiment of the present invention.

FIG. 4A depicts a partial side sectional view of the distal end of the hydraulic guidewire advancement system 10 according to another embodiment of the present invention. In FIG. 4A, the catheter 20 of FIG. 2 is coaxially disposed within a balloon catheter 70. The balloon catheter 70 includes a proximal end (not shown) and a distal end 74, and is formed as a sheath 75 having an inner surface 76 defining a lumen 77 housing the catheter 20 axially disposed therethrough. A balloon 80 is attached to the outer surface 83 of the balloon catheter 70 near the distal end 74 of the balloon catheter 70. The boundaries of the balloon 80 are defined by proximal 81 and distal 82 balloon attachment sites.

Figure 4B:
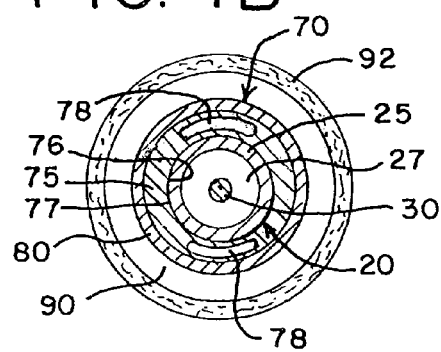
FIG. 4B is a cross-sectional view of the hydraulic guidewire advancement system depicted in FIG. 4A and taken along line 4B-4B.

In this embodiment, an additional side port (not shown) in fluid communication with one or more inflation lumen(s) 78 extending through the wall of the balloon catheter sheath 75 (not shown) is connected to the hydraulic guidewire advancement system 10 to receive pressurized fluid for inflating the balloon 80. (FIGS. 4A and 4B). The inflation lumen(s) 84 is open to the interior of the balloon 80 to complete the fluid communication of the balloon 80 with the fluid supply. Conventional fluids, such as saline, may be supplied by a suitable driver under an inflation pressure sufficient for inflating the balloon 80 and centering the catheter 20. Radiographic contrast fluids may be included for visualization purposes. The balloon 80 can be selected to have an average burst pressure between about 2 to about 20 atmospheres, preferably between about 5 to about 10 atmospheres. Those skilled in the art may readily optimize the burst pressure to a desired level.

Regarding the embodiments depicted in FIGS. 3 and 4, the distal end 24 of the catheter 20 is typically advanced through a bodily vessel 90 just proximal to an occlusion 88. At this point the balloon 80 is inflated against the surrounding vessel walls 92. This can help to center and/or stabilize the position of the catheter 20 and hydraulic guidewire 30 relative to the lesion or occlusion 88. Then, by sequential and repeated application of positive and negative pressure to the inflation lumen 42, the hydraulic guidewire 30 can be dottered, repeatedly contacting the occlusion 88 so as to clear a path through the occlusion 88 to facilitate entry of additional interventional devices therethrough, as described. An aspiration lumen (not shown) may be additionally incorporated through the sheath 75 of the balloon catheter 70 to allow for the removal of debris associated with the occlusion 88. The aspiration lumen is connected to a separate aspiration port (not shown) under vacuum pressure.

The catheter 20 may be advanced to the site of the lesion directly. Alternatively, the hydraulic guidewire advancement system 10 of the present invention may be advanced to the lesion over a previously laid conventional guidewire. This may be done by passing a catheter 20 of the present invention over the initial guidewire (without the hydraulic guidewire), and then exchanging the conventional wire for a piston-hydraulic guidewire 30. Alternatively, the sheath 25 of the catheter 20 may include an additional guidewire lumen extending therethrough, which can allow for delivery of the hydraulic guidewire advancement system 10 to the lesion over the conventional guidewire without the need for exchange.

The length of the catheter 20 may generally range from about 80 cm to about 350 cm. More preferably the catheter 20 is may range in length from about 150 cm to about 220 cm or any length sufficient to reach distant target site relative to the site of entry. The catheter 20 may be made from a variety of material components differing in size, shape, and flexibility. Preferably, the guidewire lumen 27 has an inner diameter compatible for guidewires 30 having an outside diameter ranging between about 0.05 inches to about 0.5 inches, more preferably from about 0.075 inches to about 0.35 inches, still more preferably from about 0.09 inches to about 0.15 inches.

The catheter 20 may have a substantially uniform diameter at the distal end 24 or it may be tapered. A tapered distal end 29 as depicted in FIGS. 2 to 4 can prevent the piston 40 from dislodging out of the distal end 24 of the catheter 20 and may enhance the ability of the catheter 20 to traverse through an occlusion 88 in conjunction with the hydraulic guidewire 30. Alternatively, one or more mechanical stops or obstructions can be incorporated near the distal end 24 of the catheter 20 to prevent piston egress from the distal end 24.

The guidewire 30 is typically formed as a composite structure made from flexible, elastic, bendable, kink-resistant, sterilizable, biocompatible materials to provide sufficient flexibility for traversing a patient's vasculature. A variety of different guidewires differing in core materials, core diameters, core taper, covers, tips, tip styles, extent of coiling, lubricous coatings, and radiopaque markings are known to those of skill in the art.

Preferred materials include Nitinol and stainless steel. The choice of material may depend on factors such as cost and degree of stiffness required. Nitinol is preferred for applications requiring more flexibility; stainless steel may be preferred for applications where greater stiffness is required. A Nitinol wire may be formed, for example, by drawing through dies and then ground, preferably using a center-less grinding technique. Alternatively, the guidewire may be formed from a thin spring tempered stainless steel material.

In addition, the tip 32 of the guidewire may be formed into a variety of terminal shapes or implementations for enhancing traversal and/or rupture of occlusion tissues. FIGS. 2 to 4 depict a tapered, ball shaped distal end 32, which is designed to enhance the ability of the guidewire 30 to traverse through an occlusion. Further, the tip or end 32 of the guidewire 30 may be configured for various degrees of flexibility or stiffness (with differing tip loads in grams). Exemplary commercially available guidewires include the ASAHI Miracle Bros family of guidewires (3.0 g, 4.5 g, 6.0 g, and 12.0 g; Abbott Vascular, Abbott Park, Ill.).

The outside diameter of the hydraulic guidewire 30 may generally range between about 0.005 inches to about 0.05 inches, more preferably from about 0.007 inches to about 0.038 inches, still more preferably from about 0.009 inches to about 0.015 inches. The guidewire tip diameter may generally range between about 0.009 inches to about 0.015 inches. In a particular embodiment, the guidewire end may have a rounded atraumatic spring coil tip with an outside diameter of about 0.014 inches.

A variety of different lengths, sizes and types of guidewires may be used. Given that the hydraulic guidewire 30 will be removed, whereas the catheter 20 will initially remain in place, the length of the hydraulic guidewire 30 must be longer than the length of the catheter 20 and at least long enough to facilitate its advancement beyond the distal end 24 of the catheter 20 against a target lesion or occlusion 88. Typically, the length of the guidewire 30 will be between about 175 to about 220 cm.

As described above, the hydraulic guidewire 30 is fixedly coupled to a piston 40 generally configured as a disk-shaped annular flange having a diameter snugly and perpendicularly fitting into the guidewire lumen 27. Preferably, the guidewire 30 is perpendicularly centered through the piston 40, whereby the distal end 34 of the hydraulic guidewire 30 is configured to exit through the distal end 24 of the catheter 20. The piston 40 is typically configured to be disposed in the guidewire lumen 27 near the distal end 24 of the catheter 20, generally within about 2 cm to about 10 cm from the distal end 24. The width of the piston 40 or flange may be variable and it may be further attached to a proximal portion of the guidewire 30 via a bellows or in accordance with other piston configurations known to those of skill in the art. The piston 40 may be manufactured from any suitably resilient material capable of forming a movable seal through the guidewire lumen 27. Exemplary piston materials include Teflon®, nylon, silicone, rubber, metallic materials, and the like.

The catheters 20, 70 are preferably manufactured by extrusion from conventional, medical grade, polymeric materials such as polyurethane, polyamide, polyethylene, and the like. The catheters 20, 70 and guidewires 30 of the present invention may further include lubricious coatings to enhance trackability and reduce friction. The coatings may be hydrophilic or hydrophobic in nature and may be applied, for example, to various catheter surface areas in their entirety, or be confined to the distal portions of the guidewire 30. Exemplary coatings include polytetrafluoroethylene (PTFE)-based coatings, such as Teflon® and silicone.

The balloon 80 may be formed from any suitable material known for use in interventional procedures, including but not limited to PEBAX®, nylon, Hytrel®, Arnitel® or other suitable polymers. Preferably, the balloon 80 has a generally cylindrical inflated shape defined by proximal 81 and distal 82 attachment sites, tapering with respect to the longitudinal axis of the balloon catheter 70. The balloon 80 may be attached at these locations using any suitable adhesive, such as biocompatible glue, or alternatively, using heat-shrink tubing, heat bonding, laser bonding, welding, solvent bonding, one or more tie-down bands, or the like. The inflated diameter of the balloon 80 may be selected in view of the size of vessel 90 for deployment.

Preferably, portions of the hydraulic guidewire advancement system 10 are rendered radiopaque and/or MRI compatible. Accordingly, one or more of components of the hydraulic guidewire advancement system 10, including the areas surrounding the distal end 24 of the catheter 20, the distal end 74 of the balloon catheter 70, and/or distal end 32 of guidewire 30 may include materials, fillers, marker bands or powders rendering the device components radiopaque or MRI-compatible to facilitate fluoroscopic and/or MRI-compatible imaging while inside a patient's body. Exemplary marker materials include, but not limited to, platinum, platinum-nickel, palladium, iridium, gold, silver, tungsten, tantalum, tantalum powder, stainless steel, nickel-titanium alloy, such as Nitinol, bismuth, bismuth oxychloride, barium, barium sulphate, iodine, alloys thereof, or any other suitable material known to those of skill in the art. Portions of the hydraulic guidewire advancement system 10 may be rendered more radiopaque by incorporating radiopaque marker bands or by coating, for example, a stainless steel coil or wire with gold or other known radiopaque marker materials as described above.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The inventon claimed is:
1. A hydraulic guidewire advancement system comprising:
 a catheter comprising a proximal end and a distal end, the catheter further comprising a sheath, a guidewire lumen, and a distal opening in the distal end, the distal opening being adapted to be positioned adjacent an occlusion in a body vessel;
 a proximal catheter port adapted to be positioned outside a patient's body;
 an adapter adapted to be positioned outside the patient's body, the adapter comprising a seal member;

a hydraulic guidewire coaxially disposed through the guidewire lumen and extending out of the adapter through the seal member, the hydraulic guidewire comprising a piston movably disposed in the guidewire lumen and located near the distal end of the catheter, the piston being fixedly coupled to the hydraulic guidewire and forming a seal with an interior surface of the sheath, and the seal member forming a seal with the hydraulic guidewire and the adapter; and, a hydraulic driver connected to the proximal catheter port, wherein the hydraulic driver is configured to generate hydraulic pressure against the piston to pressurize a lumen extending from the proximal catheter port and the seal member to the piston near the distal end of the catheter, the hydraulic pressure being sufficient to advance or retract the hydraulic guidewire relative to the distal end of the catheter.

2. The system of claim 1, wherein the piston comprises an annular flange, wherein the guidewire is perpendicularly centered therethrough.

3. The system of claim 1, comprising a hydraulic pressure release means facilitating removal of the guidewire and piston from the sheath.

4. The system of claim 3, wherein the adapter comprises a check flow adapter removably connected to the proximal end of the catheter and the hydraulic pressure release means comprises the check flow adapter.

5. The system of claim 4, wherein the check flow adapter comprises an opening through which the proximal portion of the guidewire is movably disposed.

6. The system of claim 1, wherein the distal end of the catheter is structurally configured to prevent egress of the piston therefrom.

7. The system of claim 1, wherein the distal end of the catheter is tapered.

8. The system of claim 1, wherein the distal end of the guidewire has a tip stiffness between about 3 grams to about 25 grams and has a tip diameter between 0.007 to 0.016 inches.

9. The system of claim 1, wherein the guidewire tip is tapered.

10. The system of claim 1, wherein the hydraulic driver comprises a syringe.

11. The system of claim 1, wherein the hydraulic driver utilizes a hydraulic fluid to generate the hydraulic pressure, and wherein the hydraulic fluid comprises saline.

12. The system of claim 1, wherein an expandable balloon is affixed to a distal portion of the sheath and wherein an inflation lumen extends through the sheath and is in fluid communication with an interior of the balloon.

13. The system of claim 1, further comprising a balloon catheter comprising:
a balloon catheter sheath having a proximal end, a distal end, a proximal balloon inflation port, and an inner surface defining a balloon catheter lumen axially disposed therethrough; and,
a balloon attached to a distal portion of the balloon catheter sheath, the balloon operably connected to the proximal balloon inflation port by at least one inflation lumen extending longitudinally through the balloon catheter sheath,
wherein the catheter is coaxially disposed through the balloon catheter lumen.

14. A method for advancing a guidewire through a lesion in a bodily lumen comprising:
a) providing a hydraulic guidewire advancement system comprising:
  i. a catheter comprising a proximal end and a distal end, the catheter further comprising a sheath, a guidewire lumen, and a distal opening in the distal end, the distal opening being adapted to be positioned adjacent an occlusion in a body vessel;
  ii. a proximal catheter port adapted to be positioned outside a patient's body;
  iii. an adapter adapted to be positioned outside the patient's body, the adapter comprising a seal member;
  iv. a hydraulic guidewire coaxially disposed through the guidewire lumen and extending out of the adapter through the seal member, the hydraulic guidewire comprising a piston movably disposed in the guidewire lumen and located near the distal end of the catheter, the piston being fixedly coupled to the hydraulic guidewire and forming a seal with an interior surface of the sheath, and the seal member forming a seal with the hydraulic guidewire and the adapter; and,
  v. a hydraulic driver connected to the proximal catheter port,
b) positioning the distal end of the catheter in a bodily lumen proximal to the lesion;
c) connecting the proximal catheter port to the hydraulic driver;
d) actuating the hydraulic driver to apply positive hydraulic pressure against the piston to pressurize a lumen extending from the proximal catheter port and the seal member to the piston near the distal end of the catheter, the hydraulic pressure being sufficient to advance the hydraulic guidewire relative to the distal end of the catheter.

15. The method of claim 14, further comprising
actuating the hydraulic driver to apply negative hydraulic pressure to the piston, thereby retracting the hydraulic guidewire in a proximal direction away the lesion and repeating the steps of advancing and retracting the hydraulic guidewire to repeatedly contact the lesion.

16. The method of claim 14, further comprising extending the distal end of the catheter and the hydraulic guidewire through the lesion.

17. The method of claim 14, further comprising the additional steps of:
a) affixing a distal portion of the sheath with an expandable balloon and providing to the sheath an inflation lumen extending therethrough and in fluid communication with an interior of the balloon; and,
b) inflating the balloon proximal to the lesion prior to actuating the hydraulic guidewire.

18. The method of claim 14, further comprising the additional steps of:
a) providing the hydraulic guidewire advancement system with a balloon catheter, the balloon catheter comprising a proximal end, a distal end, and a proximal balloon catheter port; a balloon catheter sheath having an inner surface defining a balloon catheter lumen axially disposed therethrough; and a balloon attached to a distal portion of the balloon catheter sheath, the balloon connectively linked to at least one inflation lumen connectively linked to the proximal balloon catheter port, the at least one inflation lumen extending longitudinally through the balloon catheter sheath; and
b) inflating the balloon proximal to the lesion prior to actuating the hydraulic guidewire.

19. The method of claim 14, further comprising the steps of releasing the hydraulic pressure, removing the hydraulic guidewire from the catheter, and extending a second guidewire through the catheter.

20. The method of claim 19, wherein the step of releasing the hydraulic pressure further comprises uncoupling the adapter from the proximal end of the catheter, the adapter comprising a check flow adapter.

21. The method of claim 20, further comprising coupling a second check flow adapter to the proximal end of the catheter and extending the second guidewire through the adapter and the catheter.

22. The method of claim 19, wherein the second guidewire is extended through the lesion.

23. The method of claim 22, comprising the additional steps of retaining the distal end of the second guidewire distal to the lesion, removing the remainder of the guidewire advancement system, advancing an interventional device over the second guidewire, and positioning the interventional device at a position sufficient for treating the lesion.

24. The method of claim 14, wherein the lesion comprises a chronic total occlusion.

* * * * *